United States Patent
Larkin

[11] 3,941,846
[45] Mar. 2, 1976

[54] PREPARATION OF NITROCARBONYL COMPOUNDS

[75] Inventor: John M. Larkin, Wappingers Falls, N.Y.

[73] Assignee: Texaco Inc., New York, N.Y.

[22] Filed: Apr. 19, 1971

[21] Appl. No.: 135,468

Related U.S. Application Data

[63] Continuation-in-part of Ser. No. 706,760, Feb. 20, 1968, abandoned.

[52] U.S. Cl.......... 260/593 R; 260/596; 260/601 R
[51] Int. Cl.$^2$.................. C07C 49/06; C07C 47/02
[58] Field of Search............ 260/593 R, 596, 601 R, 260/632 N

[56] References Cited
UNITED STATES PATENTS

| | | | |
|---|---|---|---|
| 2,475,996 | 7/1949 | Smith............................. | 260/632 N |
| 3,240,823 | 3/1966 | Bonetti et al. ................. | 260/632 N |
| 3,579,594 | 5/1971 | Larkin ........................... | 260/632 N |

OTHER PUBLICATIONS

Kirk–Othmer "Encyclopedia of Chemical Technology," 1st Ed., Vol. 9, pp. 375–381, Interscience (1951), N.Y.

V. V. Perekalin, "Unsat. Nitro Cmpds," pp. 4–13, (1964), Dauey, N.Y.

Vanderbilt et al., Aldehyde–Nitropar–Affincondensation, "I & EC," pp. 34–38, (1940).

Primary Examiner—Donald G. Daus
Assistant Examiner—D. B. Springer
Attorney, Agent, or Firm—T. H. Whaley; C. G. Ries; George J. Darsa

[57] ABSTRACT

A method of preparing a nitrocarbonyl having at least 4 carbon atoms corresponding to the formula:

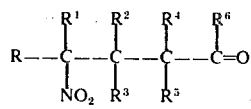

by contacting a dinitroalcohol having at least 5 carbon atoms corresponding to the formula:

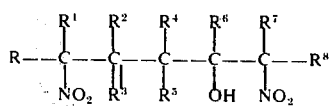

with an alkaline agent at a temperature of from about 0° to 200°C. A valuable by product recoverable from the reaction is a nitroalkane. The contemplated nitrocarbonyls include nitroketones and nitroaldehydes which are useful as solvents, plasticizers, bactericides, lubricant additives and fuel additives.

19 Claims, No Drawings

PREPARATION OF NITROCARBONYL COMPOUNDS

CROSS REFERENCE TO RELATED in part

This application is a continuation inpart of my copending application Ser. No. 706,760 filed Feb. 20, 1968, now abandoned.

This invention relates to a method for preparing nitroketones and nitroaldehydes. In particular it relates to a novel method for preparing nitroketones and nitroaldehydes from dinitroalcohols. Moreover, the process additionally provides a means for the preparation and recovery of nitromethane and other nitroalkanes as valuable by-products.

BACKGROUND OF THE INVENTION

Heretofore, nitroketones and nitroaldehydes were not generally available at low cost. Where such nitrocarbonyls were desired their manufacture from relatively expensive initial reactants was required. One prior means of producing nitroketones and nitroaldehydes was by the reaction of nitroalkanes with alpha, beta-unsaturated carbonyl compounds. Such previously known procedures, however, produced the sought after compounds in relatively poor yields such as, for example, yields of approximately 65 percent nitroketone or 40 percent or less nitroaldehyde. Moreover, the nitrocarbonyls were in many instances recovered in admixture with other products, particularly nitroalcohols and nitro-containing polymers, presenting isolation and purification difficulties. Efforts to increase purity by vacuum distillation of nitroaldehydes, for example, culminated in some instances with explosions. Such experiences, taken together with costly and not readily available starting materials, made the process commercially unattractive.

It is therefore an object of this invention to provide a method for the preparation of nitrocarbonyl compounds.

It is another object of this invention to provide a method for the preparation of nitroketones and nitroaldehydes which concomitantly provides an economical route for the production of nitroalkanes.

Yet another object of this invention is to provide a method for the preparation of nitroketones and nitroaldehydes in higher yields.

Other objects and advantages will become apparent from a reading of the following detailed description and examples.

SUMMARY OF THE INVENTION

Broadly, this invention contemplates a method of preparing a nitrocarbonyl compound having at least 4 carbon atoms which comprises contacting a dinitroalcohol having at least 5 carbon atoms and corresponding to the formula:

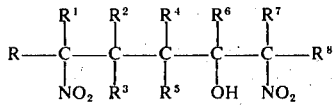

where R is hydrogen or an alkyl group having from 1 to 95, and preferably from 1 to 20 carbon atoms and where $R^1$, $R^2$, $R^3$, $R^4$, $R^5$, $R^6$, $R^7$ and $R^8$ are hydrogen or alkyl groups having from 1 to 10, preferably from 1 to 6, carbon atoms, with an alkaline agent. The contemplated nitrocarbonyls prepared according to the instant method correspond to the formula:

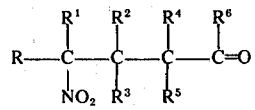

where R and $R^1$, $R^2$, $R^3$, $R^4$, $R^5$ and $R^6$ are as defined above. As can be seen, when $R^6$ is hydrogen, the ultimate carbonyl compound is a nitroaldehyde. In those instances where $R^6$ is alkyl, the carbonyl recovered is a nitroketone. In addition, the process provides as a valuable and recoverable by-product nitroalkanes corresponding to the formula:

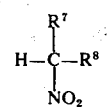

where $R^7$ and $R^8$ are as defined above.

According to this invention the contemplated nitrocarbonyls are derived from dinitroalcohols corresponding to the above formula and include such alcohols as 1,5-dinitro-2-pentanol, 1,5-dinitro-4-methyl-2-pentanol, 1,5-dinitro-3-methyl-2-pentanol, 1,5-dinitro-2,4,4-trimethyl-2-pentanol, 1,5-dinitro-2-hexanol, 1,5-dinitro-2-methyl-2-hexanol, 2,6-dinitro-3-hexanol, 1,5-dinitro-2-decanol, 1,5-dinitro-2-ethyl-2-decanol, 1,5-dinitro-2-octadecanol, 1,5-dinitro-3-methyl-2-dodecanol, 1,5-dinitro-8-ethyl-2-dodecanol, 2,6-dinitro-3-eicosanol and 1,5-dinitro-2-docosanol.

The illustrative dinitroalcohols contemplated as starting materials and listed above may be prepared for example, by contacting substituted and unsubstituted olefins having at least 5 carbon atoms such as 1-pentenes, 1-hexenes, 2-hexenes, 1-octenes, 1-octadecenes, and 4-nonenes with dinitrogen tetroxide and oxygen at temperatures of between −40° to 20°C. to form a nitroalkyl peroxynitrate. The intermediate nitroalkyl peroxynitrate is thereafter contacted with a reducing agent at a temperature of between −20° to 30°C. to form a vicinal nitroalkyl nitrate in accordance with the procedure described in U.S. Pat. No. 3,282,983. The vicinal nitroalkyl nitrate so prepared is subsequently converted to the dinitroalcohol by heating the nitrate at a temperature of at least 100°C. thereby thermally rearranging the vicinal nitroalkyl nitrate to a dinitroalcohol in accordance with the procedure described in co-pending application Serial No. 686,820 filed Nov. 30, 1967 entitled "Preparation of Dinitroalcohols", now U.S. Pat. No. 3,579,594 by John M. Larkin and assigned to the assignee hereof.

More specifically the process of this invention comprises contacting a dinitroalcohol as hereinabove defined with an alkaline agent thereby forming a nitrocarbonyl and a nitroalkane. By an alkaline agent is meant a substance capable of accepting a proton. Illustrative of the alkaline agents contemplated in the instant invention are oxides, hydroxides and salts of weak acids of the metals of Groups IA, IB, IIA, IIB, IIIA, VIIB and VIII of the periodic table. More specifically, metals contemplated herein and present as the oxide, hydroxide or salt include sodium, potassium, lithium, magnesium, calcium, strontium, barium, copper, zinc, aluminum, manganese, and cobalt. The alkaline agent in turn is exemplified by sodium acetate, sodium carbonate, sodium bicarbonate, sodium borate, sodium citrate, sodium hydroxide, potassium hydroxide, potassium acetate, potassium stearate, lithium hydroxide, magnesium oxide, magnesium oxalate, calcium oxide, calcium carbonate, calcium octoate, strontium oxide, strontium acetate, barium oxide, barium hydroxide, barium carbonate, copper stearate, cupric oxide, zinc oxide, aluminum hydroxide, alumina hydrates, aluminum acetate, manganese acetate, maganese carbonate, cobalt acetate and cobalt hydroxide. Other alkaline agents include basic nitrogen compounds illustrated by ammonia, ammonium carbonate, amines such as triethylamine and triethanolamine, quaternary ammonium hydroxides and salts as benzyltrimethylammonium hydroxide and its acetate. Preferably we employ weak alkaline agents, such as alumina and sodium acetate. When stronger alkaline agents are employed, such as sodium hydroxide and potassium hydroxide, we have found it advantageous to continously remove the by-product nitroalkane thereby providing a means for controlling reaction rates while simultaneously deterring polymer formation.

In accordance with the inventive process, the dinitroalcohol is contacted with the alkaline agent in amounts of from about 0.01 equivalents to 5.0 equivalents of agent per mole of dinitroalcohol. While the exact mechanism by which the reaction proceeds is not fully understood it is believed that the agent functions to remove a proton from the alcohol's hydroxyl group thereby initiating the cleavage reaction. When catalytic amounts of agent are employed, that is, amounts of agent ranging from about 0.01 to 0.2 equivalents of agent per mole of dinitroalcohol, the agent is believed to be regenerated by reaction with nitroalkyl anions. In those instances where reagent amounts of agent are employed, the nitroalkyl anion is converted to the corresponding nitroalkane at the conclusion of the reaction by the addition of, for example, dilute acids such as hydrochloric acid, sulfuric acid, phosphoric acid, acetic acid or formic acid. When strongly alkaline agents such as sodium or potassium hydroxide are contemplated, catalytic amounts of agent in the range stated above have been found to be preferable. When weaker alkaline agents are selected, such as alumina and sodium acetate, reagent amounts ranging from about 0.9 to 2.0 equivalents of agent per mole of dinitroalcohol are preferred.

The reaction temperature employed may vary from about 0°C. and 200°C. and preferably from about 10° to 160°C. In highly preferred embodiments, where $R^6$ is hydrogen and the desired carbonyl is a nitroaldehyde, the reaction temperature is between 100° and 160°C. Temperatures above 200°C. are generally undesirable in that such conditions promote the formation of alpha, beta-unsaturated carbonyls and polymers while temperatures below 0°C. excessively prolong reaction times. The reaction time is normally between 5 minutes and 48 hours although longer and shorter periods may be employed.

In combination with the above alkaline agent, the reaction is conducted under the prescribed temperature conditions outlined above in a non-aqueous environment. The dinitroalcohol precursor contemplated above has itself been found to be a satisfactory medium in those instances where it is a non-viscous liquid at the reaction temperatures prescribed above. Where the dinitroalcohol is a highly viscous liquid or a solid at the reaction temperature, nonaqueous diluents are employed. Applicable diluents include any non-reactive liquid hydrocarbon including for example, a wide range of $C_5$ to $C_{18}$ hydrocarbons, including hexane, heptane, octane, nonane, dodecane, 1-octene, 1-dodecene, 2,4,4-trimethyl-1-pentene, benzene, toluene, xylene, ortho-dichlorobenzene and perhalogenated alkanes. When employing a diluent, we have found it beneficial to provide the diluent in amounts ranging from about 5 to 98 weight percent diluent based on the weight of dinitroalcohol, preferably in the range of from about 40 to 90 weight percent.

Specific examples of the nitrocarbonyl compounds prepared according to the inventive process include 4-nitrobutanal, 4-nitro-3-methylbutanal, 4-nitropentanal, 4-nitroheptanal, 4-nitroundecanal, 4-nitro-6-ethyldodecanal, 3,3-dimethyl-4-nitrobutanal, 2,5,5-trimethyl-4-nitrohexanal, 4-nitroeicosanal, 5-nitro-2-pentanone, 5-nitro-2-hexanone, 4,4-dimethyl-5-nitro-2-pentanone, 1-nitro-4-heptanone, 6-nitro-3-octanone, 5-nitro-2-octanone, 5-nitro-3-methyl-2-octanone, 5-nitro-2-pentadecanone, 7-nitro-4-octadecanone and 5-nitro-2-eicosanone. In practice, yields as high as 95 percent nitroketone have been recovered while yields of greater than 60 percent nitroaldehyde may be provided. In general, nitrocarbonyl yield ranges from 65 to 95 percent.

As previously indicated, a valuable reaction by-product consists of a nitroalkane having the formula:

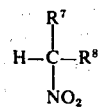

which is recovered from the reaction medium by distillation, solvent extraction or by desorption from the alkaline agent, such as alumina. Nitroalkane isolation and recovery provides yields in the range of 50 to 95 percent. Illustrative nitroalkanes prepared according to this invention include for example nitromethane, nitroethane, 1-nitropropane, 2-nitropropane, 1-nitrobutane, 2-nitrobutane, 1-nitrooctane, 4-nitrododecane and 10-nitroeicosane.

The nitrocarbonyls prepared according to this invention are useful as solvents, plasticizers, bactericides, lubricant additives, fuel additives and as intermediates for the preparation of 4-nitroalkanoic acids and 2-pyrrolidinones. The nitroalkanes are similarly useful as solvents, rocket propellants, pigment wetting agents, and as intermediates in the manufacture of hydroxylamine, soaps, emulsifiers, resins, photographic developers, pharmaceuticals and dyestuffs.

In order to more fully illustrate the nature of our invention and manner of practicing the same the following examples are presented.

EXAMPLE I

To a solution of 5.6 grams (0.05 mole) of 2,4,4-trimethyl-1-pentene in 55 milliliters of carbon tetrachloride maintained at 0°C. there was simultaneously added over a period of 4¾ hours 3.1 milliliters (0.05 mole) of dinitrogen tetroxide and 60.5 milliliters per minute of oxygen. The system was thereafter flushed with nitrogen and the flask contents cooled to approximately −5° to −10°C. Nitric oxide was bubbled through the solution at the rate of 60.5 milliliters per minute for 22 minutes. The resulting blue-green solution was stirred at approximately −10°C. for an additional 15 minutes. The solvent was subsequently removed under vacuum at room temperature and 10.79 grams of 1-nitro-2,4,4-trimethyl-2-pentyl nitrate was recovered.

A solution of 6.3 grams of 1-nitro-2,4,4-trimethyl-2-pentyl nitrate in 150 milliliters of an inert medium consisting of a linear polymer having a molecular weight of 775 with repeating $CF_2CFCl$ units was heated at 120°–130°C. for a total of 15 minutes and then was subsequently heated at 117°C. for 16 hours. The mixture was allowed to cool, and was extracted with a 150 milliliter and a 50 milliliter portion of methanol. The combined methanol extract was evaporated at reduced pressure to yield a two-phase liquid. This liquid was chromatographed on 30 grams of silica gel. There was eluted 4.36 grams of 1,5-dintro-2,4,4-trimethyl-2-pentanol in solvents consisting of methylene chloride, ether, and mixtures thereof.

To a solution of 1.0 gram of 1,5-dinitro-2,4,4-trimethyl-2-pentanol in 20 milliliters of benzene there was added 3.0 grams of alumina. The mixture was stirred and allowed to stand at room temperature for 20 hours. The alumina was removed by filtration and the filtrate was evaporated under vacuum at room temperature. A yield of 0.56 gram (72%) of a yellow liquid identified by infrared to be 5-nitro-4,4-dimethyl-2-pentanone was recovered. Nitromethane is recovered from the alumina by extraction with a mixture of ether and methanol followed by evaporation of the solvent mixture.

EXAMPLE II

A solution of 0.5 gram of 1-nitro-2,4,4-trimethyl-2-pentyl nitrate in 5 milliliters of toluene was heated at reflux for 5 hours. The solvent was removed under vacuum at 40°C. and 0.3 gram of a yellow oil was recovered and identified by infrared to be 1,5-dinitro-2,4,4-trimethyl-2-pentanol. 0.15 gram of this material was dissolved in 20 milliliters of benzene and 2 grams of alumina was added thereto. The mixture was allowed to stand for 18 hours and the alumina was thereafter removed by filtration. After evaporation of the filtrate a liquid was recovered and identified by infrared to be 5-nitro-4,4-dimethyl-2-pentanone.

EXAMPLE III

A solution of 4.7 grams of 2-methyl-1-pentene in 55 milliliters of carbon tetrachloride was maintained at 0°–4°C. while a mixture of oxygen and dinitrogen tetroxide was introduced at 60.5 milliliters per minute during a 4½ hour period. A total of 4.6 grams of dinitrogen tetroxide was thus introduced. The solution was cooled to −15°C. and was flushed with nitrogen and maintained at −10° to −15°C. while nitric oxide was introduced at 60.5 milliliters per minute during a 22 minute period. The solution was stirred for an additional 15 minutes at −10°C. and subsequently allowed to warm to room temperature and the carbon tetrachloride removed by vacuum distillation. The recovered liquid, 9.91 grams, was indicated by infrared to be 1-nitro-2-pentyl nitrate.

A solution of 3.5 grams of 1-nitro-2-methyl-2-pentyl nitrate in 100 milliliters of an inert medium consisting of a linear polymer having a molecular weight of 775 with repeating $CF_2CFCl$ units was heated at 105°C. for ½ hour, at 110°–120°C. for ½ hour, and finally at 125 to 128°C. for 2¼ hours. The dinitroalcohol and unconverted nitrate were extracted and chromatographed according to the procedures for isolation of the dinitroalcohol of Example I. A total of 1.44 gram of liquid product identified by infrared to be 1,5-dinitro-2-methyl-2-pentanol was obtained.

To a solution of 0.31 gram of 1,5-dinitro-2-methyl-2-pentanol in 50 milliliters of methanol there was added 1.5 gram of sodium acetate. The mixture was allowed to stand for 6 days. The methanol was evaporated under vacuum and a pasty orange solid remained. The solid was mixed with 50 milliliters of ether, and the solid was removed by filtration. The ether was evaporated from the filtrate to yield 0.197 gram of a yellow liquid indicated by infrared to be 5-nitro-2-pentanone.

EXAMPLE IV

From 4.95 grams of 2-methyl-1-hexene in 55 milliliters of carbon tetrachloride there was prepared 10.52 grams of 1-nitro-2-methyl-2-hexyl nitrate by introducing 4.6 grams of dinitrogen tetroxide in a stream of oxygen at 0°C. followed by nitric oxide at −10°C. as in Example I. The 1-nitro-2-methyl-2-hexyl nitrate thus prepared was purified by chromatography over silica gel.

A solution of 2.75 grams of 1-nitro-2-methyl-2-hexyl nitrate in 80 milliliters of an inert medium consisting of a linear polymer having a molecular weight of 775 with repeating $CF_2CFCl$ units was heated at 128°C. for 2¼ hours. The dinitroalcohol was extracted and chromatographed according to the procedures for isolation of the dinitroalcohol of Example I. In this manner there was obtained 1.70 gram of 1,5-dinitro-2-methyl-2-hexanol.

To a solution of 0.91 gram of 1,5-dinitro-2-methyl-2-hexanol in 25 milliliters of benzene there was added 4.2 grams of alumina. The mixture was stirred for 24 hours, and the alumina was removed by filtration. After evaporation of the filtrate there was obtained 0.29 gram of 5-nitro-2-hexanone which was identified by infrared and proton magnetic resonance.

EXAMPLE V

From 6.3 grams of 4-methyl-1-pentene in 55 milliliters of carbon tetrachloride, there was prepared 12.59 grams of 1-nitro-4-methyl-2-pentyl nitrate by introducing 6.9 grams of dinitrogen tetroxide in a stream of oxygen at 0°C. followed by nitric oxide at −10° to −15°C. according to the procedure of Example I.

A solution of 2 grams of 1-nitro-4-methyl-2-pentyl nitrate in 90 milliliters of ortho-dichlorobenzene was heated rapidly to reflux and held at 179°–180°C. for 10 minutes. A conversion of 95 percent and yield of 83 percent (6.0 grams) of the dinitroalcohol, 1,5-dinitro-4-methyl-2-pentanol, was obtained by distilling off the bulk of the solvent under vacuum and removing the remainder of the solvent by pentane extraction.

To a solution of 6.00 grams of 1,5-dinitro-4-methyl-2-pentanol in approximately 150 milliliters of xylene there was added 1.0 gram of barium oxide. The bulk of the solvent was slowly distilled off at 138°C. over a 5 hour period. Infrared indicated the presence of nitromethane in the distillate. The nitromethane is recovered by fractional distillation.

The barium oxide was removed from the residue by filtration. The remainder of the xylene was removed from the filtrate by vacuum evaporation at 55°C. 5.08 grams of a dark liquid was chromatographed on silica gel to give a 48 percent yield of 3-methyl-4-nitrobutanol corresponding to 83 percent conversion of starting material.

EXAMPLE VI

A mixture of 6.91 grams of 1,5-dinitro-4-methyl-2-pentanol and 0.3 gram of barium oxide was heated for 4¼ hours at 110°–120°C. at 6–7 millimeters pressure in an apparatus having a receiver for the collection of distillate at room temperature and a second receiver for the collection of a more volatile distillate at approximately −75°C. At the conclusion of the heating period, 3-methyl-4-nitrobutanal was found in the receiver maintained at room temperature and nitromethane was found in the second receiver maintained at −75°C.

EXAMPLE VII

An aqueous solution having a pH of 8 and consisting of 3.4 grams of potassium dihydrogen phosphate and 234 milliliters of 0.1 N sodium hydroxide in a total volume of 500 milliliters was prepared. To 100 milliliters of this solution there was added 1.1 grams of 1,5-dinitro-2-pentanol. The mixture was stirred at room temperature for 45 hours, the solution thereafter extracted with ether, and the ehter subsequently removed by evaporation. The recovered material consisted only of unconverted 1,5-dintro-2-pentanol. Chromatographic and infrared analysis confirmed the absence of 4-nitrobutanal.

EXAMPLE VIII

To a solution of 2.50 grams of 1,5-dinitro-2-pentanol in 25 milliliters of 95% ethanol-5% water there was added 5 milliliters of concentrated aqueous ammonium hydroxide. The solution became yellow, and a precipitate formed within 1½ hours. After 24 hours, the precipitate was removed by filtration. The product was identified as a nitrogen-containing polymer.

EXAMPLE IX

A solution of 16.8 grams of 4,4-dimethyl-2-(2,2-dimethylpropyl)-1-pentene in 120 milliliters of carbon tetrachloride is maintained at 0°C. and there is introduced 9.3 grams of dinitrogen tetroxide in a stream of oxygen during a 4 period. The average ratio of oxygen to dinitrogen tetroxide is 20 to 1 during the introduction. The solution is cooled to −10° to −15°C., and nitric oxide is introduced at 65 milliliters per minute during a 40 minute period. The solution is maintained at −10° to −15°C. for an additional 15 minutes, and the solution is allowed to warm to ambient temperature. The solvent is removed by evaporation in vacuum at 35°–40°C., and there remains 2,2,6,6-tetramethyl-4-nitromethyl-4-heptyl nitrate.

The 2,2,6,6-tetramethyl-4-nitromethyl-4-heptyl nitrate so prepared is dissolved in 200 milliliters of chlorobenzene and is heated at reflux for 2½ hours. The solvent is removed by vacuum distillation and there is recovered 1-nitro-2,2,6,6-tetramethyl-4-nitromethyl-4-heptanol.

A ten percent solution of 1-nitro-2,2,6,6-tetramethyl-4-nitromethyl-4-heptanol in benzene is charged to a 1½ inch diameter glass column packed with 100 grams of 80–200 mesh gamma alumina and the solution is permitted to percolate through the alumina. The benzene solution exiting from the column contains 1-nitro-2,2,6,6-tetramethyl-4-heptanone and nitromethane. The benzene and nitromethane are subsequently separated by distillation and the distillate is further fractionated thereby separately recovering nitromethane and benzene. The nitromethane is recovered as a product, and the benzene is recycled by reintroduction with additional 1-nitro-2,2,6,6-tetramethyl-4-nitromethyl-4-heptanol for percolation through the alumina containing column.

I claim:

1. A method of preparing a saturated nitrocarbonyl compound having at least 4 carbon atoms and corresponding to the formula:

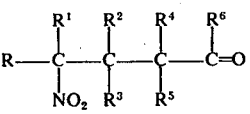

which consists essentially of contacting in a non-aqueous liquid environment a dinitroalcohol having at least 5 carbon atoms and corresponding to the formula:

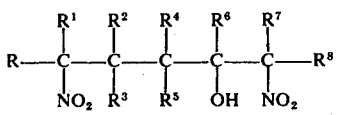

where R is hydrogen or an alkyl group having from 1 to 20 carbon atoms and where $R^{1-8}$ are hydrogen or alkyl groups having from 1 to 10 carbon atoms with an agent selected from the group consisting of oxides, hydroxides and salts of weak acids of the metals sodium, potassium, lithium, magnesium, calcium, strontium, barium, copper, zinc, aluminum, manganese and cobalt and basic nitrogen compounds consisting of ammonia, ammonium carbonate, triethylamine, triethanolamine, benzyltrimethylammonium hydroxide and benzyltrimethylammonium acetate, where said contacting is conducted at a temperature of from about 0° to 200°C. when $R^6$ is an alkyl group and at a temperature of between 100° to 160°C. when $R^6$ is hydrogen.

2. A method according to claim 1 wherein from about 0.01 to 5.0 equivalents of said agent are employed per mole of said dinitroalcohol.

3. A method according to claim 1 wherein said contacting is conducted at a temperature of from about 10° to 160°C.

4. A method according to claim 1 wherein said agent is alumina.

5. A method according to claim 1 wherein said agent is sodium acetate.

6. A method according to claim 1 wherein said agent is barium oxide.

7. A method according to claim 1 wherein said agent is sodium hydroxide.

8. A method according to claim 1 wherein said contacting is conducted in a non-aqueous non-reactive liquid hydrocarbon medium.

9. A method according to claim 8 wherein said compound is a $C_5$ to $C_{18}$ hydrocarbon.

10. A method according to claim 8 wherein said non-aqueous non-reactive liquid hydrocarbon medium is a perhalogenated alkane linear polymer having repeating $CF_2CFCl$ units and a molecular weight of 775.

11. A method according to claim 1 wherein said nitrocarbonyl compound is 5-nitro-4,4-dimethyl-2-pentanone.

12. A method according to claim 1 wherein said nitrocarbonyl compound is 5-nitro-2-pentanone.

13. A method according to claim 1 wherein said nitrocarbonyl comfound is 1-nitro-2,2,6,6-tetramethyl-4-heptanone.

14. A method according to claim 1 wherein said nitrocarbonyl compound is 5-nitro-2-hexanone.

15. A method according to claim 1 wherein said nitrocarbonyl compound is 3-methyl-4-nitrobutanal.

16. A method according to claim 1 wherein said contacting is conducted by continuously passing said dinitroalcohol over said agent.

17. A method of preparing a nitroalkane and a saturated nitrocarbonyl compound, said nitrocarbonyl compound having at least 4 carbon atoms and corresponding to the formula:

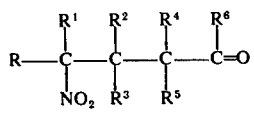

which consists essentially of:
a. contacting in a non-aqueous liquid environment a dinitroalcohol having at least 5 carbon atoms and corresponding to the formula:

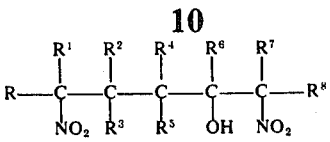

where
R is hydrogen or an alkyl group having from 1 to 20 carbon atoms and where $R^{1-8}$ are hydrogen or alkyl groups having from 1 to 10 carbon atoms with an agent selected from the group consisting of oxides, hydroxides and salts of weak acids of the metals sodium, potassium, lithium, magnesium, calcium, strontium, barium, copper, zinc, aluminum, manganese and cobalt and basic nitrogen compounds consisting of ammonia, ammonium carbonate, triethylamine, triethanolamine, benzyltrimethylammonium hydroxide and benzyltrimethylammonium acetate wherein said contacting is conducted at a temperature of from about 0° to 200°C. when $R^6$ is an alkyl group and at a temperature between 100° to 160°C. when $R^6$ is hydrogen, b. continuously separating and recovering said nitroalkane formed in step (a) from said nitrocarbonyl formed in step (a), and c. separating and recovering said nitrocarbonyl from step (b).

18. A method according to claim 17 wherein said nitroalkane is nitromethane.

19. A method according to claim 17 wherein said nitroalkane is nitroethane.

* * * * *